(12) United States Patent
Chen

(10) Patent No.: US 8,313,428 B2
(45) Date of Patent: Nov. 20, 2012

(54) SIDE-VIEWING ENDOSCOPE STRUCTURE

(75) Inventor: Sung-Nan Chen, Taoyuan County (TW)

(73) Assignee: Medical Intubation Technology Corporation, Taoyuan County (TW)

( * ) Notice: Subject to any disclaimer, the term of this patent is extended or adjusted under 35 U.S.C. 154(b) by 197 days.

(21) Appl. No.: 13/009,170

(22) Filed: Jan. 19, 2011

(65) Prior Publication Data
US 2011/0230721 A1    Sep. 22, 2011

(30) Foreign Application Priority Data
Mar. 16, 2010 (TW) ................... 99107702 A

(51) Int. Cl.
*A61B 1/04* (2006.01)
*A61B 1/06* (2006.01)
(52) U.S. Cl. ......... 600/170; 600/129; 600/175; 600/179
(58) Field of Classification Search ............. 600/109, 600/129, 170–173, 175, 176, 179; 348/65, 348/75, 76, 82–85; 356/241.5
See application file for complete search history.

(56) References Cited

U.S. PATENT DOCUMENTS

| | | | | | |
|---|---|---|---|---|---|
| 3,773,039 | A | * | 11/1973 | Mori et al. | 600/173 |
| 4,727,859 | A | * | 3/1988 | Lia | 356/241.5 |
| 5,215,077 | A | * | 6/1993 | Oku | 600/175 |
| 5,253,638 | A | * | 10/1993 | Tamburrino et al. | 600/170 |
| 5,613,936 | A | * | 3/1997 | Czarnek et al. | 600/166 |
| 5,702,249 | A | * | 12/1997 | Cooper | 433/29 |
| 5,790,185 | A | * | 8/1998 | Auzerais et al. | 348/84 |
| 5,961,445 | A | * | 10/1999 | Chikama | 600/112 |
| 6,537,209 | B1 | * | 3/2003 | Pinkhasik et al. | 600/170 |
| 6,817,976 | B2 | * | 11/2004 | Rovegno | 600/173 |
| 6,887,196 | B2 | * | 5/2005 | Arai et al. | 600/178 |
| 2010/0053312 | A1 | * | 3/2010 | Watanabe et al. | 348/65 |

* cited by examiner

*Primary Examiner* — John P Leubecker
(74) *Attorney, Agent, or Firm* — WPAT, P.C.; Anthony King

(57) ABSTRACT

A side-viewing endoscope structure includes a front tubular section, an intermediate tubular section, a rear cap and an optical imaging unit. The front tubular section includes a tube, a reflector holder, and a reflector. The tube includes a main body and a coupling portion. The reflector holder is fitted in the main body of the tube and provided on one side of an outer wall surface thereof. The reflector is arranged on the reflector holder. A length of the intermediate tubular section has a reduced outer diameter to match the coupling portion. The rear cap has a rear wall provided with a cable hole. The optical imaging unit is located in the intermediate tubular section and the rear cap, and includes a flexible printed circuit board, a camera lens, a light source and a cable so as to transmit images.

8 Claims, 4 Drawing Sheets

SIDE-VIEWING ENDOSCOPE STRUCTURE

FIELD OF THE INVENTION

The present invention relates to a side-viewing endoscope structure, and more particularly to an endoscope device that provides lateral light to capture images.

BACKGROUND OF THE INVENTION

It has become a very important diagnosis and examination technique in the modem medical treatment by extending a very thin catheter and an endoscope into a patient's body via the patient's throat and using flash light and an image capture device to capture actual images of organ deep inside the patient's body. To enable convenient directional operation of image capturing, an endoscope device that uses lateral lighting to capture images has become an applied technique that has received wide attention of people. It is known the size of the endoscope has direct relation with the discomfort suffered by a patient when the endoscope invades the patient's throat, and the endoscope for use in industrial and other purposes must also have reduced size for extending into extremely small gaps to capture images. The endoscope would have largely limited applications if it could not have minimized dimensions. Therefore, it has become a critical technical point in designing the endoscope to miniaturize the size thereof.

In the currently available techniques, a side-viewing endoscope device for capturing images in a direction perpendicular to an axis of the endoscope is configured as a two-piece hollow capsule having a front and a rear capsule. The front capsule is provided on one side of its wall with a light window, and an inclined reflector is fixedly mounted in the front capsule corresponding to the light window, so that a laterally projected light source received by the reflector is refracted into an axial direction of the capsule. Further, the front capsule is provided around a rear open end with screw threads. The rear capsule has a front open end and is provided on a rear end with a through hole for a cable to extend therethrough. An optical camera lens, a light emitting element, and a cable are fixedly serially arranged to form a unit, which is extended into and fitted in the rear capsule. The optical camera lens faces toward the reflector, and the light emitting element emits light sidewardly relative to the axis of the capsule. The rear capsule is provided around the front open end with screw threads for meshing with the screw threads on the front capsule, so that the front capsule and the rear capsule are screwed to each other to complete the two-piece capsule for the conventional side-viewing endoscope. The side-viewing endoscope with the above-described configuration has the following disadvantages:

(1) In manufacturing the currently available side-viewing endoscope using threaded connection for its front and rear capsules, spaces allowing for forming screw threads of predetermined pitch and depth must be reserved on the endoscope. By doing this, it would prevent the endoscope from being further miniaturized. Further, with the miniaturized size of the endoscope, it is difficult or even impossible to align the front and the rear capsule with each other for screwing them together. Thus, the threaded connection is not a suitable design for the miniaturized side-viewing endoscope.

(2) In the unit consisting of the fixedly and serially arranged optical camera lens, light emitting element and cable, the optical camera lens actually has an outer diameter smaller than other elements and has to be mounted at the front open end of the rear capsule. Since the unit of the optical camera lens, light emitting element and cable must be disposed in the rear capsule via the front open end thereof with the optical camera lens located at the front open end, the front open end of the rear capsule would inevitably have an inner diameter larger than the outer diameter of the optical camera lens. Therefore, an additional locating means is required to hold the optical camera lens in place at the front open end of the rear capsule.

SUMMARY OF THE INVENTION

A primary object of the present invention is to provide a side-viewing endoscope structure to overcome the problems existed in the prior art side-viewing endoscope.

To achieve the above and other objects, the side-viewing endoscope structure according to the present invention includes a front tubular section, an intermediate tubular section, a rear cap, and an optical imaging unit. The front tubular section includes a tube, a reflector holder, and a reflector. The tube includes a main body and a coupling portion. The main body is an elongated hollow shell having a beveled rear open end and a front open end provided on an upper side thereof with a first aligning and engaging portion, and the coupling portion is a ring-shaped sleeve correspondingly connected to a rear lower side of the beveled rear open end of the main body. The reflector holder is axially and immovably fitted in the main body of the tube with a beveled rear end wall of the reflector holder flushing with the beveled rear open end of the main body of the tube, and is provided on one side of an outer wall surface thereof with a second aligning and engaging portion corresponding to the first aligning and engaging portion on the main body of the tube. The reflector is correspondingly arranged on the beveled rear end wall of the reflector holder. The intermediate tubular section is a long tubular shell having a front and a rear open end. A length of the intermediate tubular section at the front open end has a reduced outer diameter to match an inner diameter of the coupling portion of the tube, so as to fitly insert into the coupling portion and become fixed thereto. The intermediate tubular section is provided on one side of a peripheral wall thereof with a through opening to serve as a light window. The rear cap is an enclosure having a front open end for correspondingly extending into the rear open end of the intermediate tubular section, and has a rear wall that is provided with a cable hole. The optical imaging unit is axially extended into and fixedly located in the intermediate tubular section and the rear cap; and includes a flexible printed circuit board, a camera lens located at a front end of the flexible printed circuit board to correspondingly immovably fit in the front open end of the intermediate tubular section, a light source component located on the flexible printed circuit board behind the camera lens to correspond to the light window provided on the intermediate tubular section, and a cable for transmitting images connected to a rear part of the flexible printed circuit board and rearward extended through the cable hole on the rear cap.

When assembling the side-viewing endoscope structure of the present invention, the optical imaging unit can be disposed in the intermediate tubular section from the rear open end thereof, and the camera lens can be correspondingly immovably fitted in the inner diametrically reduced front open end of the intermediate tubular section. This design allows the intermediate tubular section of the side-viewing endoscope structure of the present invention to be sized in complete correspondence to that of the optical imaging unit to thereby save the space occupied by the intermediate tubular section, enabling the side-viewing endoscope structure to have a minimized volume. Further, in the present invention, the coupling portion of the front tubular section and the rear cap are firmly connected to two ends of the intermediate tubular section without using any threaded connection. Therefore, unlike the prior art side-viewing endoscope including two mutually screwed capsules that cause difficulty in further reduction of the overall volume of the endoscope and could not be quickly aligned and assembled due to the small size thereof, the side-viewing endoscope structure of the present invention can have effectively reduced overall volume to largely relieve the patient's discomfort when the endoscope passes through the patient's throat for examining the inside of the patient's body. The side-viewing endoscope structure according to the present invention can also be advantageously applied in industrial and other purposes for detection in an extremely small space.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

The present invention will now be described with a preferred embodiment thereof and with reference to the accompanying drawings. It is understood the accompanying drawings are illustrated only for assisting in describing the present invention and are not necessarily in compliance with the exact or precise size proportion and part arrangement of a real product manufactured through implementing the present invention. Therefore, the size proportion and part arrangement shown in the accompanying drawings are not intended to limit the present invention, which is intended to be limited only by the appended claims.

Figure 1:
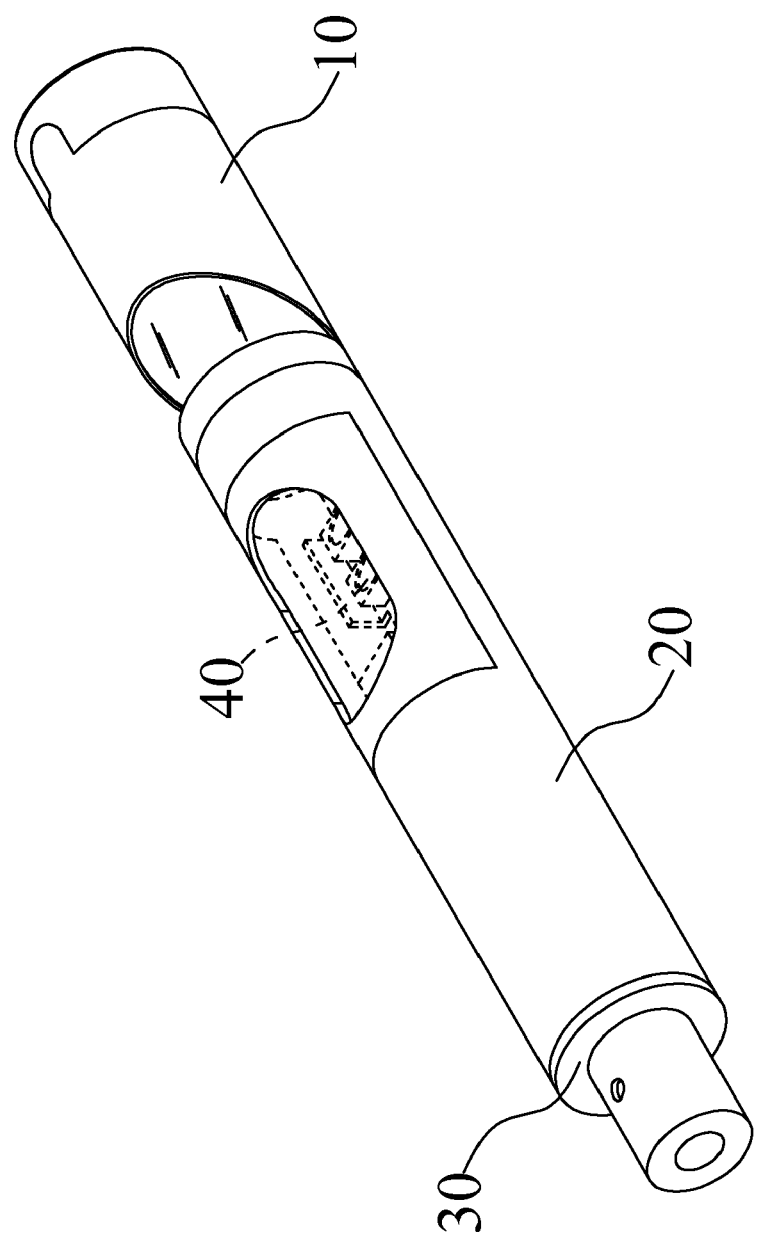
FIG. 1 is an assembled rear perspective view of a side-viewing endoscope structure according to the present invention.
Figure 2:
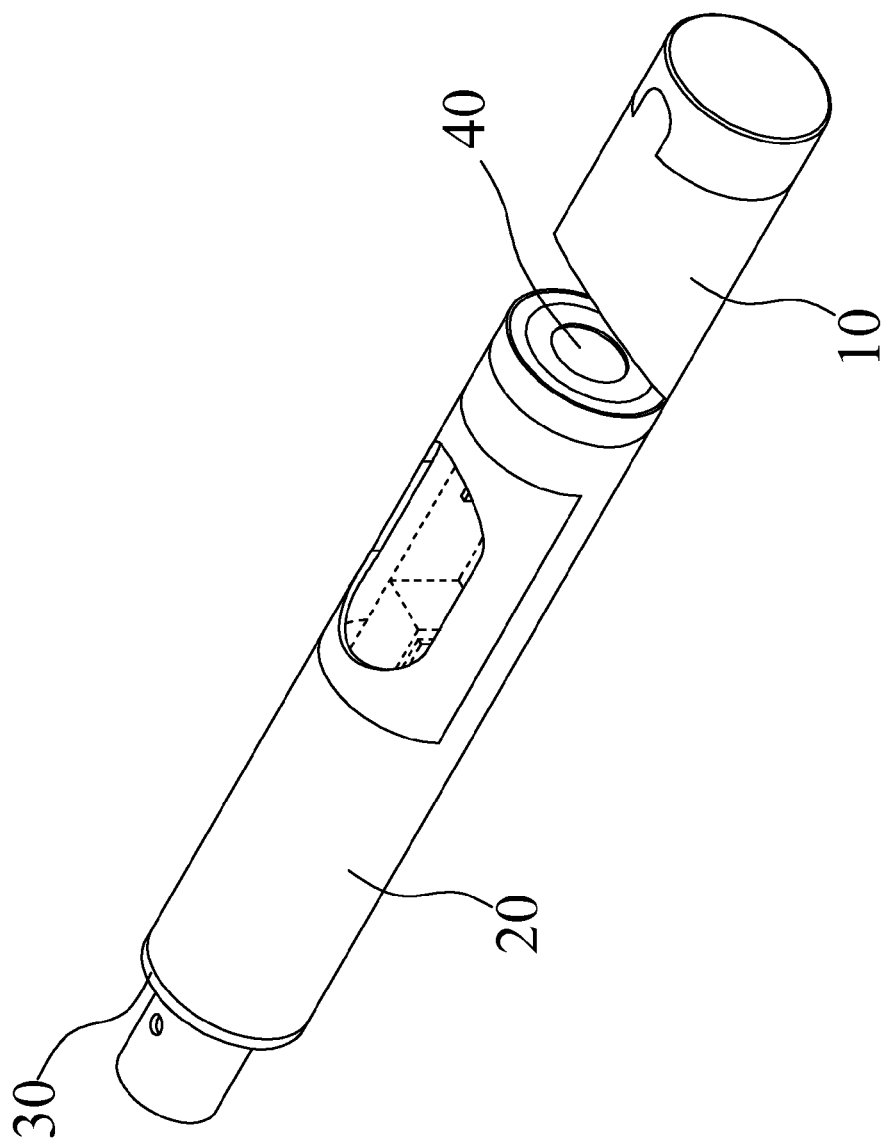
FIG. 2 is an assembled front perspective view of the side-viewing endoscope structure according to the present invention.
Figure 3:
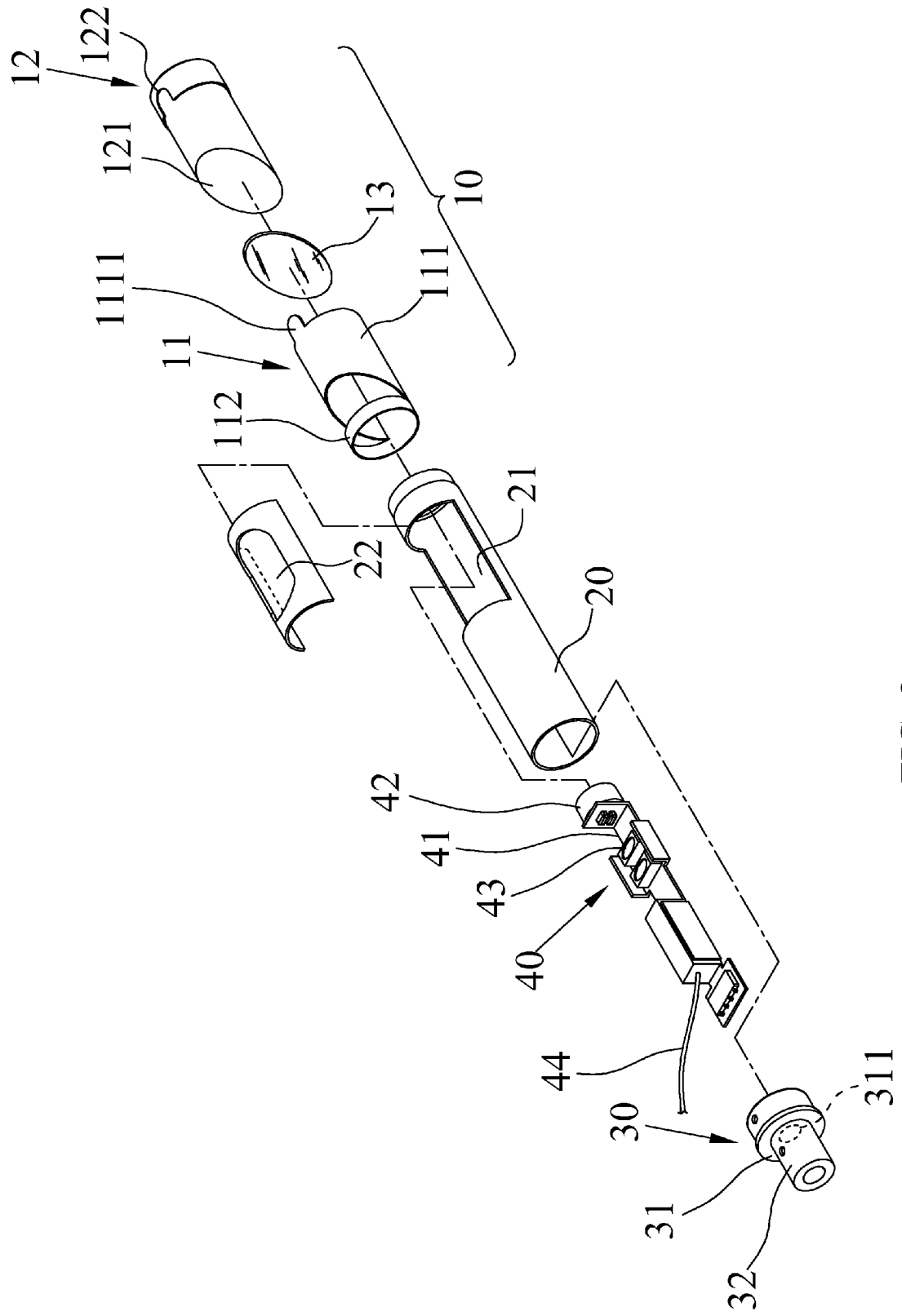
FIG. 3 is an exploded perspective view of the side-viewing endoscope structure according to the present invention.
Figure 4:
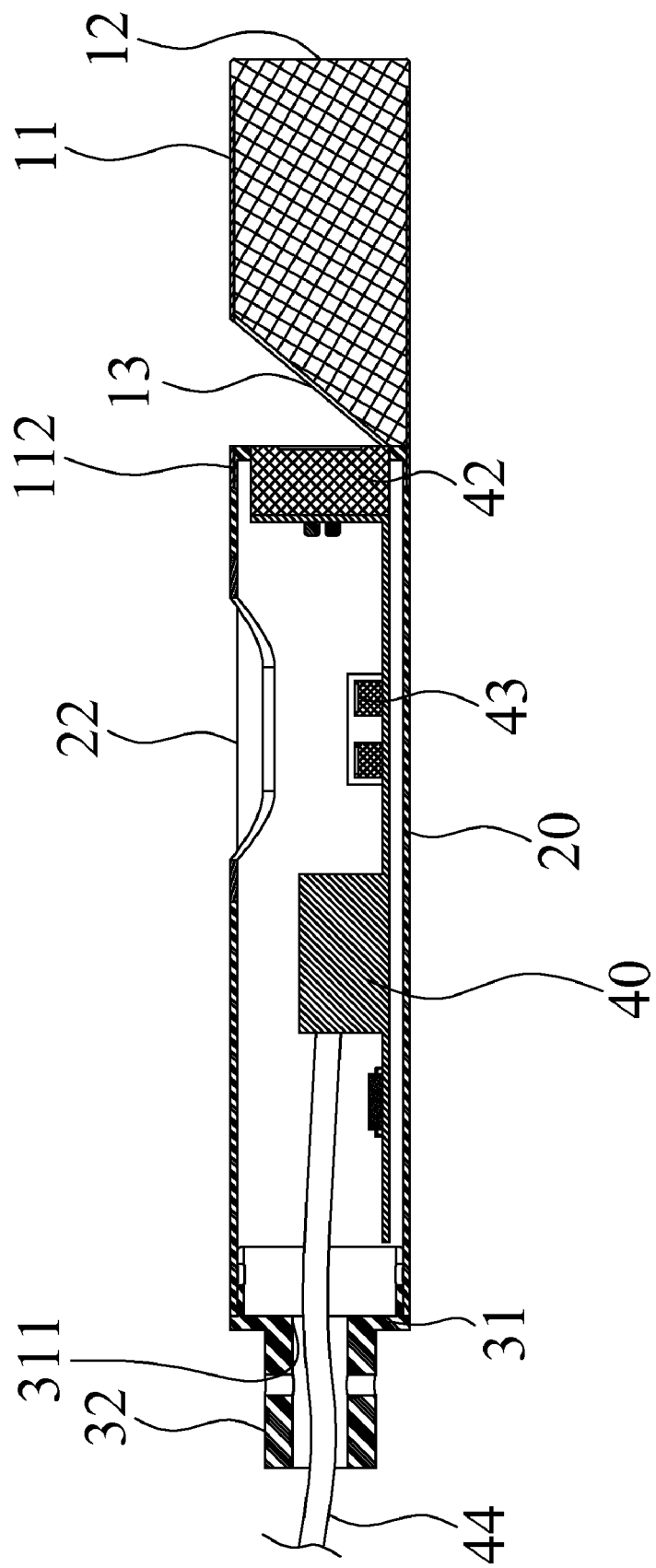
FIG. 4 is an assembled sectional side view of the side-viewing endoscope structure according to the present invention.

Please refer to FIGS. 1 to 4, in which a side-viewing endoscope structure according to an embodiment of the present invention is shown. As shown, the side-viewing endoscope structure of the present invention includes a front tubular section 10, an intermediate tubular section 20, a rear cap 30, and an optical imaging unit 40.

The front tubular section 10 includes a tube 11, a reflector holder 12, and a reflector 13.

The tube 11 includes a main body 111 and a coupling portion 112. The main body 111 is an elongated hollow cylindrical shell having a beveled rear open end. The beveled rear open end of the main body 111 may have an inclination angle ranged between 30 and 60 degrees. The main body 111 has a front open end, on an upper side of which a first aligning and engaging portion 1111 is formed. In the illustrated embodiment, the first aligning and engaging portion 1111 is in the form of a forward projection. The coupling portion 112 is in the form of a ring-shaped sleeve being correspondingly connected to a rear lower side of the beveled rear open end of the main body 111.

The reflector holder 12 is axially and immovably fitted in the main body 111 of the tube 11 with a beveled rear end wall 121 of the reflector holder 12 flushing with the beveled rear open end of the main body 111 of the tube 11. The reflector holder 12 is provided on one side of an outer wall surface thereof with a second aligning and engaging portion 122 corresponding to the first aligning and engaging portion 111 on the main body 111 of the tube 11. In the illustrated embodiment of the present invention, the second aligning and engaging portion 122 is in the form of a rear-opened recess. By aligning and engaging the projection 1111 with the recess 122, a user can quickly and correctly fitting the reflector holder 12 in the tube 11.

The reflector 13 is correspondingly arranged on the beveled rear end wall 121 of the reflector holder 12, so that light laterally projected onto the reflector 13 is refracted by the reflector 13 toward the coupling portion 112.

The intermediate tubular section 20 is a long tubular shell having a front and a rear open end. A length of the intermediate tubular section 21 at the front open end has a reduced outer diameter to match an inner diameter of the coupling portion 112, so as to fitly insert into the coupling portion 112 and become fixed thereto. A glue material or other equivalent sealing means may be applied on a contact surface between the intermediate tubular section 20 and the coupling portion 112 to secure the connection of them to each other. The intermediate tubular section 20 is provided on one side of a peripheral wall thereof with a through opening to serve as a light window 21. A transparent hood 22 is fixedly mounted on the light window 21 to cover the same.

The rear cap 30 is an enclosure having a front open end for correspondingly extending into the rear open end of the intermediate tubular section 20. Again, a glue material or other equivalent sealing means may be applied on a contact surface between the intermediate tubular section 20 and the rear cap 30 to secure the connection of them to each other. The rear cap 30 has a rear wall 31 that is provided with a cable hole 311 for a cable to extend therethrough. A portion of the rear wall 31 surrounding the cable hole 311 is rearward extended to provide a cable guide 32.

The optical imaging unit 40 is axially extended into and fixedly located in the intermediate tubular section 20 and the rear cap 30. The optical imaging unit 40 includes a flexible printed circuit board 41, a camera lens 42 located at a front end of the flexible printed circuit board 41 to correspondingly immovably fit in the front open end of the intermediate tubular section 20 with a front end of the camera lens 42 flushing with the front open end of the intermediate tubular section 20, a light source component 43 located on the flexible printed circuit board 41 behind the camera lens 42 to correspond to the light window 21 provided on the intermediate tubular section 20, and a cable 44 for transmitting images connected to a rear part of the flexible printed circuit board 41 and rearward extended through the cable hole 311 and the cable guide 32 on the rear cap 30 to connect to an image display instrument.

The present invention is characterized in that, when assembling the side-viewing endoscope structure, the optical imaging unit 40 can be disposed in the intermediate tubular section 20 from the rear open end thereof, and the camera lens 42 can be correspondingly immovably fitted in the inner diametrically reduced front open end of the intermediate tubular section 20. This design allows the intermediate tubular section 20 of the side-viewing endoscope structure of the present invention to be sized in complete correspondence to that of the optical imaging unit 40 without causing any waste of the space in the intermediate tubular section 20. Thus, the side-viewing endoscope structure of the present invention can have a minimized volume. Further, in the present invention, the coupling portion 112 of the front tubular section 10 and the rear cap 30 are firmly connected to two ends of the intermediate tubular section 20 without using any threaded connection. Therefore, unlike the prior art side-viewing endoscope including two mutually screwed capsules that cause difficulty in further reduction of the overall volume of the endoscope and could not be quickly aligned and assembled due to the small size thereof, the side-viewing endoscope structure of the present invention can have effectively reduced overall volume to largely relieve the patient's discomfort when the endoscope passes through the patient's throat for examining the inside of the patient's body. The side-viewing endoscope structure according to the present invention can also be advantageously applied in industrial and other purposes for detection in an extremely small space. Therefore, the present invention is highly practical for use to create good gains.

The present invention has been described with a preferred embodiment thereof and it is understood that many changes and modifications in the described embodiment can be carried out without departing from the scope and the spirit of the invention that is intended to be limited only by the appended claims.

What is claimed is:

1. A side-viewing endoscope structure, comprising:
    a front tubular section including a tube, a reflector holder, and a reflector;
        the tube including a main body and a coupling portion;
            the main body being an elongated hollow shell having a beveled rear open end and a front open end provided on an upper side thereof with a first aligning and engaging portion; and the coupling portion being a ring-shaped sleeve correspondingly connected to a rear lower side of the beveled rear open end of the main body;
        the reflector holder being axially and immovably fitted in the main body of the tube with a beveled rear end wall of the reflector holder flushing with the beveled rear open end of the main body of the tube; and the reflector holder being provided on one side of an outer wall surface thereof with a second aligning and engaging portion corresponding to the first aligning and engaging portion on the main body of the tube; and
        the reflector being correspondingly arranged on the beveled rear end wall of the reflector holder;
    an intermediate tubular section being a long tubular shell having a front and a rear open end; a length of the intermediate tubular section at the front open end having a reduced outer diameter to match an inner diameter of the coupling portion of the tube, so as to fitly insert into the coupling portion and become fixed thereto; and the intermediate tubular section being provided on one side of a peripheral wall thereof with a through opening to serve as a light window;
    a rear cap being an enclosure having a front open end for correspondingly extending into the rear open end of the intermediate tubular section; and the rear cap having a rear wall that is provided with a cable hole; and
    an optical imaging unit being axially extended into and fixedly located in the intermediate tubular section and the rear cap; the optical imaging unit including a flexible printed circuit board, a camera lens located at a front end of the flexible printed circuit board to correspondingly immovably fit in the front open end of the intermediate tubular section, a light source component located on the flexible printed circuit board behind the camera lens to correspond to the light window provided on the intermediate tubular section, and a cable for transmitting images connected to a rear part of the flexible printed circuit board and rearward extended through the cable hole on the rear cap.

2. The side-viewing endoscope structure as claimed in claim 1, wherein a contact surface between the front open end of the intermediate tubular section and an inner wall surface of the coupling portion on the front tubular section is applied with a glue material to secure the connection of the intermediate tubular section and the coupling portion to each other; and a contact surface between an outer surface of the front open end of the rear cap and an inner surface of the rear open end of the intermediate tubular section is applied with a glue material to secure the connection of the intermediate tubular section and the rear cap to each other.

3. The side-viewing endoscope structure as claimed in claim 2, wherein the first aligning and engaging portion on the main body of the tube of the front tubular section is a forward projection, and the second aligning and engaging portion on the reflector holder is a rear-opened recess.

4. The side-viewing endoscope structure as claimed in claim 3, wherein the camera lens included in the optical imaging unit has a front end flushing with the front open end of the intermediate tubular section.

5. The side-viewing endoscope structure as claimed in claim 4, wherein the light window provided on the intermediate tubular section is covered by a transparent hood.

6. The side-viewing endoscope structure as claimed in claim 5, wherein a portion of the rear wall of the rear cap surrounding the cable hole is rearward extended to provide a cable guide.

7. The side-viewing endoscope structure as claimed in claim 6, wherein the beveled rear open end of the main body of the tube included in the front tubular section has an inclination angle ranged between 30 and 60 degrees.

8. The side-viewing endoscope structure as claimed in claim 7, wherein the front tubular section, the intermediate tubular section, and the rear cap respectively have an outer periphery with a circular cross section.

* * * * *